Figure 1:
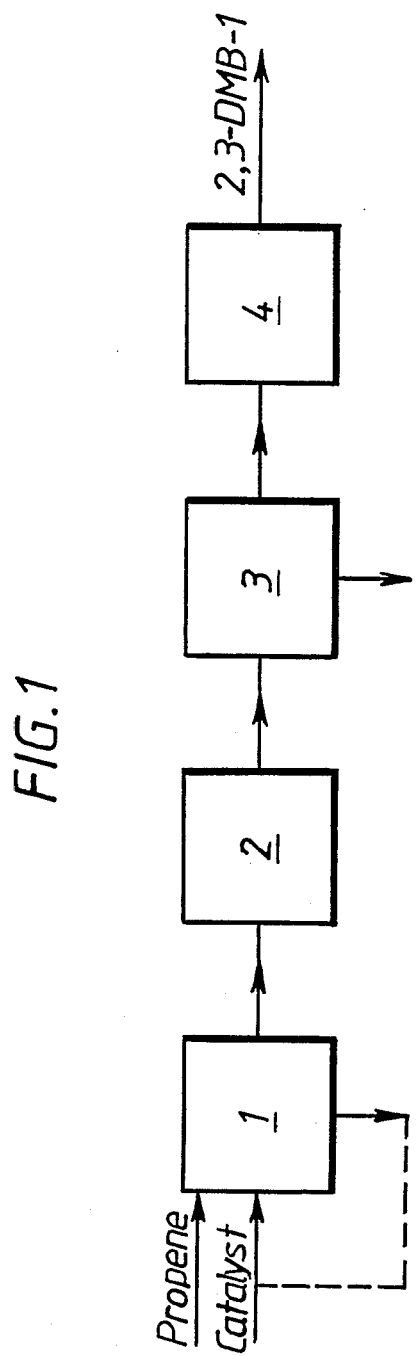

United States Patent [19]

Kent et al.

[11] Patent Number: 4,835,328

[45] Date of Patent: May 30, 1989

[54] PROCESS FOR THE PRODUCTION OF 2,3-DIMETHYLBUTENE-1 FROM PROPENE

[75] Inventors: Alexander G. Kent, Beverley; Malcolm J. Lawrenson, Swanland; Derek K. Macalpine, Haywards Heath, all of England

[73] Assignee: BP Chemicals Limited, London, England

[21] Appl. No.: 184,399

[22] Filed: Apr. 21, 1988

[30] Foreign Application Priority Data

Apr. 23, 1987 [GB] United Kingdom ............... 8709648

[51] Int. Cl.$^4$ ............................................. C07C 2/24
[52] U.S. Cl. .................................. 585/329; 585/513; 585/664; 585/668
[58] Field of Search ............... 585/329, 513, 664, 668

[56] References Cited

U.S. PATENT DOCUMENTS

| | | | |
|---|---|---|---|
| 3,204,009 | 8/1965 | Keith | 585/664 |
| 3,326,866 | 6/1967 | Haag | 585/668 |
| 3,467,726 | 9/1969 | Griffin | 585/513 |
| 3,482,001 | 12/1969 | Eberhardt | 585/513 |
| 3,686,352 | 8/1972 | Neal et al. | 585/329 |
| 3,920,765 | 11/1975 | Frech et al. | 585/664 |
| 4,288,643 | 9/1981 | Weber et al. | 585/664 |

FOREIGN PATENT DOCUMENTS 1264404 2/1972 United Kingdom ............... 585/329

OTHER PUBLICATIONS

Chemical Abstracts vol. 78, 1973, p. 328, 135624n.

*Primary Examiner*—Curtis R. Davis
*Attorney, Agent, or Firm*—Nixon & Vanderhye

[57] ABSTRACT

2,3-dimethylbutene-1 (2,3-DMB1) is produced from propene by a process comprising the steps of:
(A) converting propene in one or more stages to a product comprising 2,3-dimethylbutene-2 (2,3-DMB-2) under conditions whereby the proportion of 2,3-DMB-2 in the product is maximised,
(B) separating 2,3-DMB-2 from the product of step (A), and
(C) contacting the 2,3-DMB-2 separated in step (B) with a catalyst active for the isomerisation of 2,3-DMB-2 to 2,3-DMB-1 under conditions whereby 2,3-DMB-2 is isomerised to 2,3-DMB-1.

14 Claims, 2 Drawing Sheets

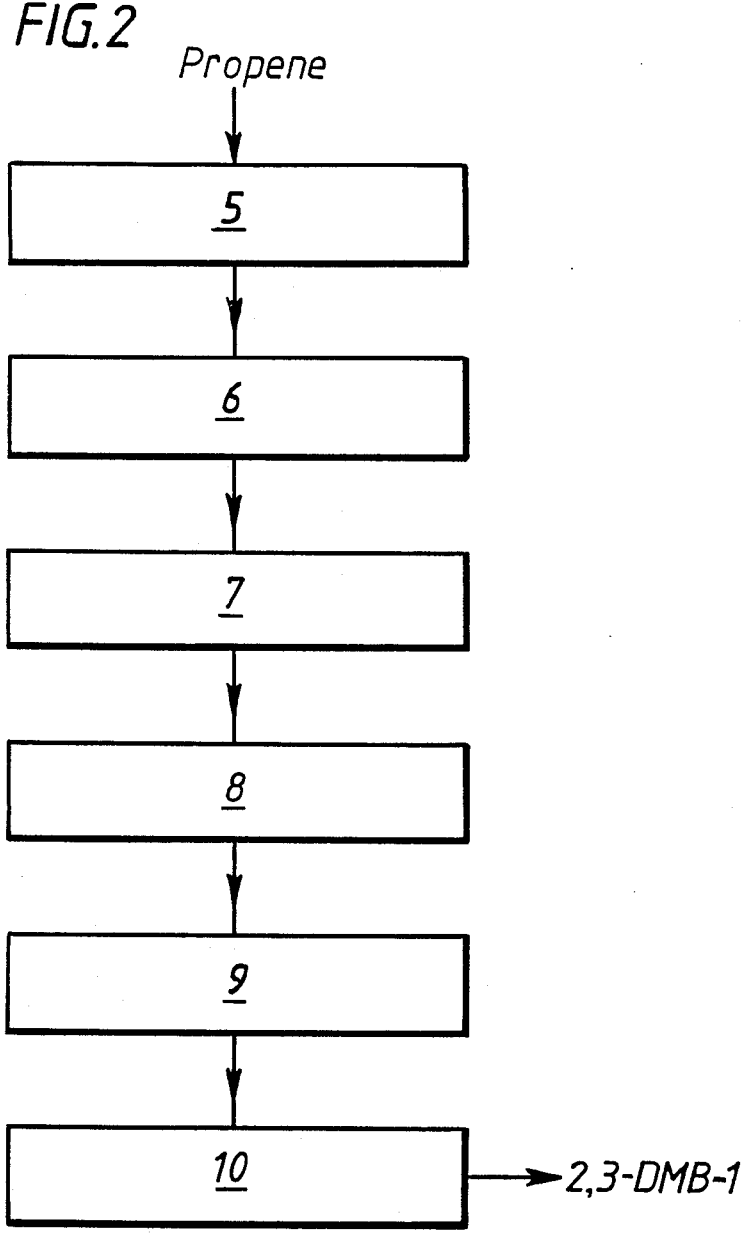

PROCESS FOR THE PRODUCTION OF 2,3-DIMETHYLBUTENE-1 FROM PROPENE

The present invention relates to a process for the production of 2,3-dimethylbutene-1 (2,3-DMB-1) from propene.

It is known from U.S. Pat. No. 4,542,249 to produce dimethylbutenes by (a) reacting diisobutylene and ethylene under disproportionation conditions to produce neohexene and (b) subjecting the total disproportionation reaction effluent containing neohexene without separation to skeletal isomerisation to form dimethylbutenes.

It is also known to produce a mixture of 2,3-dimethylbutene isomers, i.e. 2,3-DMB-1 and 2,3-dimethylbutene-2 (2,3-DMB-2) by the catalytic dimerisation of propene.

Thus, U.S. Pat. No. 3,686,352 discloses a process for the production of dimethylbutenes by dimerising in the absence of air and moisture a propylene-containing fluid in the presence of a dimerisation catalyst under reaction conditions sufficient to dimerise at least 90 percent by weight of said propylene to $C_6$ olefins, said dimerisation being carried out in the presence of a solvent having a boiling point of at least 175° F., isomerising the $C_6$ olefin mixture, separating the isomerised mixture into a methylpentene-rich stream and a dimethylbutene-rich stream, maintaining the temperature of the olefin mixture below 200° F. during the dimerisation, isomerisation and separation steps and recycling the catalyst to the dimerisation step. In this process no effort is made to separate the dimethylbutenes product into its individual isomers.

The dimerisation of propene produces not only dimethylbutenes but also methylpentenes, as demonstrated in the aforesaid U.S. Pat. No. 3,686,352, and also hexenes. Because of their relative boiling points it is difficult to separate by distillation 2,3-DMB-1 from certain of the other dimerisation products, for example 4-methylpentene-1 (4-MP-1), 3-methylpentene-1 (3-MP-1), cis-4-methylpentene-2 (cis-4-MP-2) and trans-4-methylpentene-2 (trans-4MP-2).

We have now devised a process for the production of 2,3-DMB-1 from propene which minimises the problem of separating 2,3-DMB-1 from other dimerisation reaction products.

Accordingly the present invention provides a process for the production of 2,3-DMB-1 from propene which process comprises the steps of:
(A) converting propene in one or more stages to a product comprising 2,3-DMB-2 under conditions whereby the proportion of 2,3-DMB-2 in the product is maximised,
(B) separating 2,3-DMB-2 from the product of step (A), and
(C) contacting the 2,3-DMB-2 separated in step (B) with a catalyst active for the isomerisation of 2,3-DMB-2 to 2,3-DMB-1 under conditions whereby 2,3-DMB-2 is isomerised to 2,3-DMB-1.

An advantage of operating in the manner according to the invention is that lower boiling $C_6$ olefins, 2,3-DMB-2 being the highest boiling, can readily be distilled off, thereby leaving 2,3-DMB-2, a precursor of 2,3-DMB-1 by isomerisation.

In step (A) of the process according to the invention propene is converted in one or more stages to a product comprising 2,3-DMB-2. The principal objective in step (A) is to produce 2,3-DMB-2 at the highest achievable selectivity. This may be accomplished in one or more stages. Thus in one stage propene may be contacted with a dimerisation catalyst which is selective for the production of 2,3-dimethylbutenes, preferably one which is selective for the production of 2,3-DMB-2. Suitable dimerisation catalysts are described in a review by B. Bogdanovic in Adv. Organometallic Chem. 1979, 17, 105. A suitable catalyst for conversion of propene to 2,3-DMB-2 is one based on nickel/phosphines, further details of which may be obtained from the aforesaid review article.

Alternatively, step (A) may be accomplished in two stages, for example in a first stage (i) contacting propene with a dimerisation catalyst to produce a product comprising 2,3-DMB-1 and 2,3-DMB-2 and in a second stage (ii) contacting the product from stage (i) with an isomerisation catalyst active for the isomerisation of 2,3-DMB-1 to 2,3-DMB-2 under conditions which maximise the isomerisation of 2,3-DMB-1 to 2,3-DMB-2. A suitable catalyst for dimerising propene selectively to 2,3-DMB-1 in the liquid phase is nickel acetylacetonate/tricyclohexylphosphine/ethylaluminium dichloride, though a variety of other catalysts may be employed. A suitable isomerisation catalyst for isomerising 2,3-DMB-1 to 2,3-DMB-2 is a supported alkali metal, for example sodium or potassium, though again a variety of other catalysts may be employed. Another suitable class of isomerisation catalyst for isomerising 2,3-DMB-1 to 2,3-DMB-2 is the strongly acidic macroporous cation exchange resins, particularly such cation exchange resins containing sulphonic acid groups. Examples of suitable cation exchange resins useful in the performance of the invention include Bayer Catalysts K2631 and K2634 and Amberlyst (RTM) 15.

Step (A) may be carried out in the liquid phase or the gaseous phase and either batchwise or continuously, the preferred mode of operation generally being determined by the overall economics of the process.

The temperatures and pressures to be utilised in operation of step (A) may vary widely. The preferred conditions will largely be determined by the mode of operation, the requirement for high selectivity to 2,3-dimethylbutenes and the overall process economics.

In a preferred embodiment of the present invention step (A) comprises the stages:
(I) contacting propene in the liquid phase with a dimerisation catalyst comprising nickel/phosphine/alkylaluminium at a temperature in the range from −30° to =50° C. and a pressure in the range from atmospheric to 25 bar to produce a product comprising propene dimers, including 2,3-DMB-1, and higher boiling materials.
(II) deactivating the catalyst of stage (I),
(III) separating by distillation the propene dimers from high boiling materials and catalyst residues from stage (II), and
(IV) contacting the propene dimers separated in stage (III) in the liquid phase with a heterogeneous isomerisation catalyst capable of isomerising 2,3-DMB-1 to 2,3-DMB-2.

In stage (I) of the preferred embodiment the nickel/phosphine/alkylaluminium catalyst may suitably be nickel acetylacetonate/tricyclohexylphosphine/ethylaluminium dichloride, though other catalysts described in the aforesaid review may be employed. The temperature is preferably from −10° to +10° C., more preferably about 0° C. The pressure is preferably from atmospheric to 10 bar. Whilst it may be convenient in laboratory scale operation of the process to operate at atmospheric pressure, in practice commercial operation may desirably be effected at elevated pressure in order to maintain an adequate concentration of propene in the liquid phase.

In stage (II) the catalyst used in stage (I) is deactivated. Deactivation of the catalyst is desirable in order to mimimise or eliminate further undesirable reactions during the separation stages. Deactivation may suitably be accomplished by contacting the catalyst with any material capable of decomposing or chelating with any of the catalyst components. Suitable materials include anhydrous ammonia, aqueous ammonia, amines, for example alkylamines such as triethylamine, water, aqueous strong inorganic bases, for example sodium hydroxide or potassium hydroxide, and aqueous mineral acids, for example dilute hydrochloric acid.

In stage (IV) it is preferred to use as the isomerisation catalyst a strongly acidic macroporous cation exchange resin, particularly one containing sulphonic acid groups, for example Bayer Catalysts K2631 and K2634, or Amberlyst (RTM) 15. Before use in the process, it is preferred to activate the resin, suitably by drying. Drying may be achieved by a variety of methods, for example either by heating at elevated temperature, generally about 100° C. at either atmospheric or subatmospheric pressure, or by contact with a stream of hot gas or by contact with a drying solvent.

Operation of step (A) will provide a product principally comprising 2,3-DMB-2, together with one or more of 2,3-DMB-1, methylpentenes and hexenes.

In step (B) of the process 2,3-DMB-2 is separated, suitably by distillation from the product of step (A). This may be accomplished by conventional distillation techniques. The distillation is simplified in that 2,3-DMB-2, being the highest boiling component of the product mixture, is readily recovered as a base fraction, the remainder of the product being taken off as an overhead fraction. Any overhead fraction containing 2,3-DMB-1 may, if desired, be recovered and recycled to the isomerisation stage of step (A).

In step (C) of the process the 2,3-DMB-2 separated in step (B) is contacted with a catalyst active for the isomerisation of 2,3-DMB-2 to 2,3-DMB-1. Isomerisation of 2,3-DMB-2 will generally produce an equilibrium mixture of the two isomers, i.e. 100% conversion to 2,3-DMB-1 is not generally posssible under normal conditions in a single stage isomerisation.

It is preferred to use a heterogeneous cayalyst in step (C), thereby facilitating its separation from reactants and products. As the olefin isomerisation catalysts there may be employed a supported alkali metal catalyst, an advantage of such catalysts being that they offer good activity at ambient and sub-ambient temperatures. Examples of suitable alkali metals include sodium, potassium and lithium and mixtures thereof. A preferred alkali metal is sodium. The support may suitably be a refractory oxide, for example silica, alumina, silica-alumina, magnesia, titania, ceria, or the like. Metal oxides are preferred. A preferred support is alumina. Another preferred olefin isomerisation catalyst is a strongly acidic macroporous cation exchange resin of the type as hereinbefore described.

The supported alkali metal catalyst may be prepared by any conventional technique, for example by direct addition of the alkali metal to the support at a temperature above the melting point of the alkali metal under an inert atmosphere. The catalyst may suitably comprise from 0.1 to 50%, preferably from 1.0 to 25% w/w of the alkali metal based on the weight of the support. Other preferred catalysts are Bayer Catalysts K2631 and K2634 and Amberlyst (RTM) 15.

A preferred catalyst for use in step (C) of the process is a strongly acidic macroporous cation exchange resin.

Step (C) may be carried out either in the liquid phase or the vapour phase and may be operated either batch-wise or continuously, the preferred mode of operation generally being determined by the overall economics of the process.

The temperatures and pressures employed in step (C) may vary widely. The preferred conditions will largely be determined by the mode of operation, the desirability for high selectivity to 2,3-DMB-1 and the overall process economics. Generally the use of atmospheric pressure will be found suitable. Regarding temperature, the optimum operating temperature will depend inter alia on whether the process is operated in the liquid phase or the vapour phase. In the liquid phase at atmospheric pressure, for example, in order to maximise the conversion of 2,3-DMB-2 to 2,3-DMB-1 it is preferred to operate at temperatures up to about 73° C.

The product from step (C) of the process comprises 2,3-DMB-1 and 2,3-DMB-2. The 2,3-DMB-1 may be separated and recovered from the product by distillation, though other methods of separation may be employed. The product remaining after recovery of 2,3-DMB-1 may suitably be recycled to step (C) of the process. Alternatively, the distillative recovery of 2,3-DMB-1 may be incorporated into step (C) of the process.

The process of the invention will now be further illustrated by reference to the accompanying Figures, in which FIG. 1 is a flow diagram illustrating one embodiment of the invention and FIG. 2 is a schematic block diagram illustrating a preferred embodiment of the invention, and by reference to the following Examples.

With reference to FIG. 1, 1 is a propene dimerisation and product work-up zone, 2 is an isomerisation zone, 3 is a 2,3-DMB-2 recovery zone and 4 is a 2,3-DMB-2 isomerisation zone.

In operation propene and catalyst solution are fed to the propene dimerisation unit of zone 1 wherein it is dimerised to a $C_6$ product comprising 2,3-DMB-1, 2,3-DMB-2 and possibly also methylpentenes and hexenes and $C_9$ and higher products. In the product work-up unit of zone 1 the $C_6$ product is separated from $C_9$ and higher products and catalyst which is recycled to zone 1. The $C_6$ products from zone 1 are passed to the isomerisation zone containing a heterogeneous isomerisation catalyst wherein 2,3-DMB-1 is isomerised to 2,3-DMB-2. A portion of the $C_6$ products may, however, be recycled to zone 1 as solvent for the catalyst. This zone may be omitted, particularly when 2,3-DMB-2 is produced in high selectivity in zone 1. The product from zone 2 rich in 2,3-DMB-2 is passed to the 2,3-DMB-2 recovery zone 3 wherein other $C_6$ products are distilled off. The 2,3-DMB-2 remaining is passed to the isomerisation zone 4 containing a heterogeneous isomerisation catalyst wherein 2,3-DMB-2 is isomerised to 2,3-DMB-1. The 2,3-DMB-1 is separated from the isomerisation product from zone 4 in a distillation zone (not shown) and the separated 2,3-DMB-2 recycled to zone 4. Alternatively, the distillative recovery of 2,3-DMB-1 may be incorporated into the isomerisation zone 4.

With reference to FIG. 2, 5 is a propene dimerisation zone, 6 is a product work-up zone, 7 is a distillation zone, 8 is a $C_6$ olefin isomerisation zone, 9 is a distillation zone and 10 is an isomerisation zone.

In operation propene and catalyst solution are fed to the propene dimerisation zone 5 wherein it is dimerised to a $C_6$ product comprising 2,3-DMB-1, 2,3-DMB-2 and possibly also methylpentenes and hexenes and $C_9$ and higher products. In the product work-up zone 6 the catalyst used in zone 5 is deactivated. $C_6$ olefins are separated by distillation from deactivated catalyst residues and $C_9$ and higher products in zone 7. In zone 8 the $C_6$ product separated in zone 7 is isomerised by contact with a heterogeneous isomerisation catalyst to produce a 2,3-DMB-2 rich stream. In zone 9 $C_6$ olefins are separated by distillation from 2,3-DMB-2. Finally, in zone 10 2,3-DMB-2 is isomerised by contact with a heterogeneous isomerisation catalyst to 2,3-DMB-1, which is recovered by distillation.

In the following Examples:

Example A illustrates the preparation of a 10% (nominal loading) sodium on alumina isomerisation catalyst.

Example B illustrates the preparation of a 3% (nominal loading) potassium on alumina isomerisation catalyst.

Example C illustrates the activation of a Bayer Catalyst K2631 (a cation exchange resin).

Example D illustrates the activation of an Amberlyst (RTM) 15 resin.

Example 1 illustrates propene dimerisation to 2,3-DMB-1 in the presence of a nickel acetylacetonate/-tricyclohexylphosphine/ethyaluminium dichloride catalyst system.

Example 2 illustrates $C_6$ olefin recovery from the dimerisation product (composed of catalyst, propylene oligomers and $C_6$ olefins).

Example 3 illustrates propene dimerisation in n-heptane at 0° C.

Example 4 illustrates propene dimerisation in n-heptane at 10° C.

Example 5 illustrates propene dimerisation in $C_6$ olefins at 0° C.

Example 6 illustrates propene dimerisation in heptane at 4.5 barg.

Example 7 illustrates distillation of the reaction product from Example 3.

Example 8 illustrates isomerisation of a $C_6$ olefin mixture over a sodium on alumina catalyst.

Example 9 illustrates isomerisation of 2,3-DMB-1 over Bayer Catalyst K2631.

Example 10 illustrates isomerisation of a $C_6$ olefin mixture over Bayer Catalyst K2631.

Example 11 illustrates isomerisation of a $C_6$ olefin mixture over Bayer Catalyst K2634.

Example 12 illustrates isomerisation of 2,3-DMB-1 over Amberlyst (RTM) 15.

Example 13 illustrates 2,3-DMB-2 recovery from a $C_6$ olefin mixture.

Examples 14 to 17 illustrate the batch isomerisation of 2,3-DMB-1 and 2,3-DMB-2 using a potasium on alumina catalyst and a sodium on alumina catalyst.

Example 18 illustrates the effect of temperature on the isomerisation of 2,3-DMB-2 using a sodium on alumina catalyst.

Example 19 illustrates isomerisation of 2,3-DMB-2 and recovery of 2,3-DMB-1 by distillation.

Example 20 illustrates the isomerisation of 2,3-DMB-2 over Bayer Catalyst K2631 and recovery of 2,3-DMB-1 by distillation.

CATALYST PREPARATION

Example A-10% Sodium on Alumina

A 3 necked 2 liter round bottom flask was fitted with a vacuum line, nitrogen supply line, a stirrer gland and, stirrer shaft with a stainless steel blade.

The apparatus was housed in a fluidised sand bath. The flask was purged out with nitrogen before use.

The flask was charged with 200 g of ⅛" gamma-alumina spheres (Norton SA6273) and heated under vacuum for 16 hours at 350° C. Sodium metal (22 g) was then added at 350° C. under nitrogen with stirring.

After 4 hours at 350° C. the catalyst was cooled to room temperature and transferred to a clean, dry flask, where it was stored until required.

Analysis of the free alkali metal content was determined by water hydrolysis and found to be 8.3% w/w Na.

Example B-3% Potassium on Alumina

As described in Example A except 100 g of 300–500 μm particle size gamma-alumina 11.1 g of potassium were used. The catalyst thus formed and was then diluted with a further 200 g of 300–500 μm particle size gamma-alumina. The free alkali metal content was found to be 3.0% w/w K.

CATALYST ACTIVATION

Example C

Bayer Catalyst K2631 (a cation exchange resin) was dried at 105° C./600 mm Hg for 17 hours.

Example D

Amberlyst (RTM) 15 (a cation exchange resin) was dried at 105° C./600 mm Hg for 17 hours.

Example 1

A 5 necked flanged 600 ml round bottom flask reactor was fitted with a low-pressure propene supply line, a thermowell with thermometer, a small pressure-equalised dropping funnel, rubber septum cap, and a mechanical agitator. The reactor was housed in a stirred cooling bath. The apparatus was purged with dry nitrogen before use.

3.9 ml of a 0.02M solution of nickel acetylacetonate/-tricyclohexylphosphine (1:1 molar ratio) in toluene and 74 ml of n-heptane were added to the reactor. The solution was then cooled to −10° C. A 0.95M n-heptane solution of ethyl aluminium dichloride (2.0 ml) was added via the dropping funnel at the same time as propene was passed through the reaction mixture. After the addition was complete the temperature was brought to 20° C. and kept at this temperature for 210 minutes with continuous addition of propene. The reaction was terminated by the addition of anhydrous ammonia followed by the addition of 50 ml of 1.0M aqueous sodium hydroxide.

Samples from the reactor were removed every 30 minutes, via the rubber septum cap, and shaken with a solution of sodium hydroxide. The reaction product samples were analysed by gas-liquid chromatography.

The maximum observed conversion of propene was 10.5 Kg. hr.−1 (g of Ni)−1 with a selectivity to $C_6$'s of 72%, of which 63% were 2,3-dimethylbutenes. The maximum observed productivity to 2,3-dimethylbutenes was 4.6 kgh$^{-1}$ (g of Ni)$^{-1}$ at a 2,3-DMB-1 to 2,3-DMB-2 ratio of 63:1.

Example 2

The procedure was as that described in Example 1 except that after 210 minutes the propene supply was stopped and the mixture cooled to $-10°$ C. The cooled funnel was then removed and a seven plate 1 inch Oldershaw column with still head, thermometer, condenser and distillate collecting flasks were fitted. The reactor was then heated up to 98° C. (base temperature) and the fraction between 58 ° and 73° C. (distillation head temperature) was collected.

Analysis of the distilled product (78.2 g) showed that 92% of the $C_6$ olefins produced in the dimerisation reaction had been collected overhead.

Example 3

A 5-necked flanged 20 liter flask reactor was fitted with low pressure propene and nitrogen supply lines, a thermocouple, rubber septum cap, a vent outlet and a mechanical agitator. The reactor was placed in a cooling bath and the apparatus was purged with dry nitrogen before use. The reactor was cooled to $-15°$ C. and heptane (4.0liters) and a 1.0M solution of ethyl aluminium dichloride (0.07 liters) were charged to the reactor. The mixture was then saturated with propene and a 0.02M solution (0.209 liters) of nickel acetylacetonate and tricyclohexylphosphine in toluene was added with stirring.

As the reaction started the propene flow was increased to meet the reaction demand and the pressure in the flask was maintained at 0.3 barg. The initial exotherm was used to raise the temperature of the reactor to 0°C., which was then maintained at 0° C.±2° C. during the course of the reaction.

After 7 hours the reaction was terminated by the gradual addition of water (0.003 liters) to the flask at between 0 ° and 5° C.

Analysis of the reaction mixture by gas-liquid chromatography showed it to contain 26% of 2,3-DMB-1 and 2,3-DMB-2. Selectivity to 2,3-DMB-1 and 2,3-DMB-2 was 55% based on propene. The productivity to 2,3-dimethylbutenes was 1.04 Kgh$^{-1}$ (g of Ni)$^{-1}$.

Example 4

The procedure of Example 3 was repeated except that (i) a reaction temperature of +10° C. was used and (ii) the reaction was terminated after 3 hours.

Analysis of the reaction mixture showed it to contain 21.6% 2,3-DMB-1 and 2,3-DMB-2. Selectivity to 2,3-DMB-2 was 50% based on propene.

Example 5

The procedure of Example 3 was repeated except that (i) a $C_6$ olefin mixture (1.0 liters) was used in place of heptane, (ii) 0.040 instead of 0.070 liters of a 1.0M solution of ethyl aluminium dichloride in heptane was used and (iii) 0.078 instead of 0.209 liters of a 0.02M solution of nickel acetylacetonate and tricyclohexylphosphine in toluene was used.

Analysis of the reaction mixture showed it to contain 32.4% 2,3-DMB-1 and 2,3-DMB-2. Selectivity to 2,3-DMB-1 and 2,3-DMB-2 was 47% based on propene. The productivity to 2,3-dimethylbutenes was 1.44 Kgh$^{-1}$ (g of Ni)$^{-1}$.

Example 6

A 1 liter autoclave was cooled to $-5°$ C., charged with n-heptane (100 ml) and a 1.0M solution (2.7 ml) ethyl aluminium dichloride in heptane, under propene. The autoclave was then charged with a 0.02M solution (5.4 ml) of nickel acetylacetonate and tricyclohexylphosphine (1:1 molar ratio) in toluene. Propene was then added at 4.5 barg and the reaction was maintained at 8° C.±2° C. for 2 hours.

Analysis of the reaction mixture by gas-liquid chromatography showed it to contain circa 34% 2,3-DMB-1 and 2,3-DMB-2. Selectivity to 2,3-DMB-1 and 2,3-DMB-2 was circa 46% based on propene. The productivity to 2,3-dimethylbutenes was circa 16 Kgh$^{-1}$ (g of NI)$^{-1}$.

Example 7

A reaction mixture (2.909 Kg, prepared as for Example 3) was distilled using a 40 plate 1 inch Oldershaw column. The column was initially maintained at total reflux for 3 hours and then product was taken off at a reflux ratio of 1:1 (approximate rate of take off was 1.0 liters hour$^{-1}$). The distillation was continued until all the $C_6$ components had been removed from the distillation column kettle.

The fractions were combined to give a $C_6$ olefin fraction (1.969 kg) and a residue fraction (0.700 kg) which included the distillation column kettle residues. Mass accountability was 92% with a 78% recovery of $C_6$ olefins in the combined distilled fractions.

Example 8

Two portions of 1.5 g of 25% sodium on alumina catalyst (Norton SA6273 alumina) were mixed under argon with an approximate equal volume of olefin mixture (3 ml) comprising 32% $C_6$'s with initial composition shown in Table 1. One portion was kept at 0° C. for 10 minutes the other at ca 15° C. and analysed after 10 minutes and 2 days.

TABLE 1

| Olefin (% of $C_6$) | Initial Concentrations | 10 mins at 0° C. | 10 mins at ca 15° C. | 2 days at ca 15° C. |
|---|---|---|---|---|
| 4-MP-1 | 0.5 | 2.5 | 0.8 | — |
| 2,3-DMB-1 | 70.8 | 58.5 | 21.8 | 4.0 |
| Cis-4-MP-2 | 11.3 | 7.1 | 2.9 | 0.3 |
| Trans-4-MP-2 | 5.7 | 8.9 | 13.8 | 1.9 |
| 2-MP-1 | 6.4 | 7.3 | 0.8 | 2.3 |
| Cis-Hexene-3 | — | 0.2 | 0.5 | 0.6 |
| 2-MP-2 | 1.2 | 4.8 | 7.1 | 21.1 |
| Trans-Hexene-2 | 1.6 | 1.5 | 1.6 | 1.7 |
| Cis-Hexene-2 | 1.3 | 1.0 | 0.6 | 0.4 |
| 2,3-DMB-2 | 1.2 | 13.2 | 49.9 | 67.7 |

In the Table the following abbreviations are used:
4-MP-1 — 4-methypentene-1,
2,3-DMB-1 — 2,3-dimethylbutene-1
Cis-4-MP-2 — cis-4-methylpentene-2,
Trans-4-MP-2 — trans-4-methylpentene-2,
2-MP-1 — 2-methylpentene-1,
2-MP-2 — 2-methylpentene-2
2,3-DMB-2 — 2,3-dimethylbutene-2

Example 9

2,3-DMB-1 (20 g) was placed into a 50 ml flask fitted with a reflux condenser and rubber septum and maintained under a nitrogen atmosphere. The flask was heated to 40° C. and Bayer Catalyst K2631 (0.20 g) activated according to Example C was added. Samples were taken at regular intervals and analysed by gas-liquid chromatography. Table 2 shows the results obtained.

Example 10

The procedure of Example 9 was repeated except that a mixture of 2,3-DMB-1 (48.1% w/w), t-4MP-2 (11.2%), 2-MP-1 (3.5%), 2-MP-2 (22.2%), t-hexene-2 (4.4%) and 2,3-DMB-2 (10.5%) was used in place of 2,3-DMB-1 and the reaction temperature was 50° C. Table 3 shows the results obtained.

Example 11

A reactor (of 10:1 length to diameter ratio) was packed with Bayer catalyst K2634 (16.7 ml). A feed containing a mixture of propene dimers was passed over the catalyst at a flow rate of 334 ml/hour at 50° C. Analysis of the feed and product streams is shown in Table 4.

Example 12

The procedure of Example 9 was repeated except that instead of the Bayer Catalyst K2631 resin there was used Amberlyst (RTM) 15 resin activated according to the procedure of Example D.

Table 2 shows the results obtained.

TABLE 2

| Sample | Time (seconds) | 2,3-DMB-1 (%) Example 9 | 2,3-DMB-1 (%) Example 12 |
|---|---|---|---|
| 1 | 0 | 92.5 | 92.4 |
| 2 | 420 | 81.5 | — |
| 3 | 600 | — | 81.8 |
| 4 | 1200 | 68.0 | 73.0 |
| 5 | 1620 | 61.2 | — |
| 6 | 1800 | — | 65.2 |
| 7 | 2340 | 52.1 | — |
| 8 | 2400 | — | 58.3 |
| 9 | 3000 | — | 52.2 |
| 10 | 3600 | — | 47.3 |
| 11 | 3960 | 38.1 | — |
| 12 | 4680 | 32.6 | — |

TABLE 3

| Time (seconds) | 2,3-DMB-1 | t-4-MP-2 | 2-MP-1 | 2-MP-2 | t-HEX-2 | 2,3-DMB-2 | Highers |
|---|---|---|---|---|---|---|---|
| 0 | 48.1 | 11.2 | 3.5 | 22.2 | 4.4 | 10.5 | 0.1 |
| 1440 | 15.9 | 11.2 | 3.4 | 22.2 | 4.5 | 42.7 | 0.1 |
| 4920 | 7.5 | 11.2 | 3.3 | 22.5 | 3.9 | 51.1 | 0.5 |
| 8220 | 5.8 | 11.4 | 3.3 | 22.5 | 3.7 | 52.5 | 0.8 |
| 11820 | 5.5 | 11.3 | 3.3 | 21.9 | 4.0 | 52.6 | 1.4 |
| 15420 | 5.4 | 11.0 | 3.2 | 21.9 | 3.7 | 53.5 | 1.3 |
| 19020 | 5.5 | 11.2 | 3.2 | 21.2 | 3.3 | 52.9 | 1.7 |
| 20820 | 5.4 | 11.0 | 3.1 | 21.4 | 4.0 | 53.6 | 1.5 |
| 24420 | 5.5 | 11.1 | 3.1 | 21.2 | 3.8 | 52.9 | 2.4 |

2,3-DMB-1 = 2,3-dimethylbutene-1
T-4-MP-2 = Trans-4-methylpentene-2
2-MP-1 = 2-methylpentene-1
2-MP-2 = 2-methylpentene-2
t-HEX-2 = Trans-hexene-2
2,3-DMB-2 = 2,3-dimethylbutene-2

TABLE 4

| Component | Feed % w/w | Product % w/w |
|---|---|---|
| 4-methylpentene-1 | 1.0 | 1.0 |
| 2,3-dimethylbutene-1 } cis-4-methylpentene-2 | 39.2 | 9.1 |
| trans-4-methylpentene-2 | 21.4 | 21.5 |
| 2-methylpentene-1 | 4.0 | 2.3 |
| cis-hexene-3 | 1.0 | 1.0 |
| 2-methylpentene-2 | 3.5 | 3.5 |
| trans-hexene-2 | 13.5 | 14.9 |

TABLE 4-continued

| Component | Feed % w/w | Product % w/w |
|---|---|---|
| cis-hexene-2 | 0.9 | 0.9 |
| 2,3-dimethylbutene-2 | 13.5 | 43.7 |
| Heptane | 2.0 | 2.0 |

Example 13

Batch distillation of 628 g of a $C_6$ olefin mixture (wt % composition: 4MP-1,1.1; 2,3-DMB-2/Cis 4-MP-2, 16.2; trans 4MP-2, 8.9;4MP-1/hexene-1,2.2; hexene-3, 0.4;2MP-2, 25.6; trans hexene-2,1.2; Cis hexene-2,0.2; 2,3-DMB-2,44.0) was carried out on a 1 inch 40 plate Oldershaw column with a 2 liter kettle. The lower boiling olefins (4MP1, 2,3-DMB1, c-4MP2, t4MP2, hexene-1 and 2MP1) were removed with a reflux ratio set at 20:1 which was slowly increased to 40:1 resulting in very little loss of 2,3-DMB-2 in the distillate. The 2MP2 was removed with a reflux ratio set at 60:1. Overall, this gave 90% recovery of the 2,3-DMB-2 (kettle product) with purity of 99.0%. The major impurities were cis-hexene-2 less than 0.1%, 2MP2 0.5%, trans-hexene-2 0.2% and cis-hexene-2 0.2%.

Examples 14 to 17

Portions of sodium or potassium on alumina were mixed and shaken under an inert atmosphere with small volumes of 2,3-DMB-1 or 2,3-DMB-2. The results obtained are shown in Table 5. Isomerisation of 2,3-DMB-1 produced an exothermic reaction in both cases.

TABLE 5

| Example | 14 | 15 | 16 | 17 |
|---|---|---|---|---|
| Olefin Reactant volume (ml) | 2,3-DMB1 3.0 | 2,3-DMB1 5.0 | 2,3-DMB2 3.0 | 2,3-DBM2 5.0 |
| Catalyst weight (g) | 10% Na/Al$_2$O$_3$ 1.5 | 3% K/Al$_2$O$_3$ 1.4 | 10% Na/Al$_2$O$_3$ 1.5 | 3% K/Al$_2$O$_3$ 3.4 |
| Duration (mins) | 10 | 15 | 10 | 50 |
| Product |  |  |  |  |
| (2,3DMB1) | 21% | 11.2% | 3.6% | 5.8% |
| (2,3DMB1) | 79% | 88.8% | 96.4% | 94.2% |

Example 18

Pure 2,3-DMB-2 was passed over a fixed 2 ml catalyst bed of 25% sodium on alumina at a liquid hourly space velocity of one for six hours each at 0° C., 20° C. and 45° C. Analysis of the products showed they contained 4.8%, 6.4% and 8.1%, 2,3-DMB-1 respectively.

This Example shows that 2,3-DMB-2 conversion increases with reaction temperature.

Example 19

1.5 kg of 2,3-DMB-2 and 0.15 kg of 10% sodium on alumina (prepared as Example A) were placed in the kettle of a 40 plate 1 inch Oldershaw distillation column. 2,3-DMB-1 of high purity (99.9%) was obtained at a reflux ratio of 20:1 at a rate of 25 g/hour. The head temperature was 57° C. and the kettle temperature was 73° C.

Example 20

A 10 liter 3 neck distillation kettle was fitted with a 47 plate 2 inch Oldershaw column and a liquid outlet line to a pump which circulated the distillation kettle contents over a heated catalyst bed before returning the contents to the kettle through an inlet line.

The kettle was charged with 2,3-DMB-2 (5.937 kg) and the catalyst bed with Bayer Catalyst K2631 activated as in Example C. The pump was then used to circulate the kettle contents over the catalyst bed at 50° C. at a rate of 1.2 liters hour$^{-1}$. The concentration of 2,3-DMB-1 in the kettle gradually increased to about 5.5% after 36 hours, at which point the flask temperature was raised and the distillation column brought to total reflux. After 5 hours the heads take-off was commenced at a reflux ratio of 60:1. 2,3-DMB-1 was taken off at a rate of 15 to 30 ml hour$^{-1}$ at a purity of greater than 99% (by gas-liquid chromatographic analysis).

We claim:

1. A process for the production of 2,3-dimethylbutene-1 (2,3-DMB-1) from propene which process comprises the steps of:
   (A) converting propene in one or more stages to a product comprising 2,3-dimethylbutene-2 (2,3-DMB-2) under conditions whereby the proportion of 2,3-DMB-2 in the product is maximised,
   (B) separating 2,3-DMB-2 from the product of step (A), and
   (C) contacting the 2,3-DMB-2 separated in step (B) with a catalyst active for the isomerisation of 2,3-DMB-2 to 2,3-DMB-1 under conditions whereby 2,3-DMB-2 is isomerised to 2,3-DMB-1.

2. A process according to claim 1 wherein step (A) is effected in one stage in which propene is contacted with a dimerisation catalyst which is selective for the production of 2,3-DMB-2.

3. A process according to claim 1 wherein step (A) is effected in two stages in which in a first stage (i) propene is contacted with a dimerisation catalyst to produce a product comprising 2,3-DMB-1 and 2,3-DMB-2 and in a second stage (ii) the product from stage (i) is contacted with an isomerisation catalyst active for the isomerisation of 2,3-DMB-1 to 2,3-DMB-2 under conditions which maximise the isomerisation of 2,3-DMB-1 to 2,3-DMB-2.

4. A process according to claim 1 wherein step (A) comprises the stages:
   (I) contacting propene in the liquid phase with a dimerisation catalyst comprising nickel/phosphine/alkylaluminium at a temperature in the range from −30° to +50° C. and a pressure in the range from atmospheric to 25 bar to produce a product comprising propene dimers, including 2,3-DMB-1, and higher boiling materials.
   (II) deactivating the catalyst of stage (I),
   (III) separating by distillation the propene dimers from high boiling materials and catalyst residues from stage (II), and
   (IV) contacting the propene dimers separated in stage (III) in the liquid phase with a heterogeneous isomerisation catalyst capable of isomerising 2,3-DMB-1 to 2,3-DMB-2.

5. A process according to claim 4 wherein the dimerisation catalyst is nickel acetylacetonate/tricyclohexyl phosphine/ethylaluminium dichloride.

6. A process according to claim 4 wherein the temperature in stage (I) is in the range from −10° to +10° C.

7. A process according to claim 4 wherein in stage (II) the catalyst of stage (I) is deactivated by treatment with either anhydrous ammonia, aqueous ammonia, an alkylamine, water, and aqueous strong inorganic base or an aqueous mineral acid.

8. A process according to claim 4 wherein in stage (IV) of step (A) or in step (C) the isomerisation catalyst is a supported alkali metal.

9. A process according to claim 8 wherein the alkali metal is either sodium or potassium and the support is alumina.

10. A process according to claim 4 wherein in stage (IV) of step (A) or in step (C) the isomerisation catalyst is a strongly acidic macroporous cation exchange resin.

11. A process according to claim 10 wherein the resin contains sulphonic acid groups.

12. A process according to claim 10 wherein the resin is activated by drying before use.

13. A process according to claim 1 wherein 2,3-DMB-1 is recovered from the product from step (C) comprising 2,3-DMB-1 to 2,3-DMB-2 by distillation and the remainder of the product is recycled to step (C).

14. A process according to claim 12 wherein the distillate recovery of 2,3-DMB-1 is incorporated into step (C).

* * * * *